United States Patent

Iwashita et al.

(10) Patent No.: US 11,826,186 B2
(45) Date of Patent: Nov. 28, 2023

(54) IMAGE PROCESSING APPARATUS, IMAGE PROCESSING METHOD, AND PROGRAM (71) Applicant: CANON KABUSHIKI KAISHA, Tokyo (JP)

(72) Inventors: Atsushi Iwashita, Tokyo (JP); Akira Tsukuda, Kawasaki (JP); Kosuke Terui, Yokohama (JP); Sota Torii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 69 days.

(21) Appl. No.: 16/812,605

(22) Filed: Mar. 9, 2020

(65) Prior Publication Data
US 2020/0205755 A1   Jul. 2, 2020

Related U.S. Application Data (63) Continuation of application No. PCT/JP2018/026121, filed on Jul. 11, 2018.

(30) Foreign Application Priority Data

Oct. 6, 2017   (JP) ................. 2017-196397

(51) Int. Cl.
A61B 6/00   (2006.01)
(52) U.S. Cl.
CPC .......... *A61B 6/4241* (2013.01); *A61B 6/4035* (2013.01); *A61B 6/482* (2013.01); *A61B 6/5211* (2013.01); *A61B 6/5258* (2013.01)

(58) Field of Classification Search
CPC ... A61B 6/4241; A61B 6/4035; A61B 6/5211; A61B 6/5258; A61B 6/482; A61B 6/4233; A61B 6/00; G01V 5/0041; H04N 5/32
See application file for complete search history.

(56) References Cited

U.S. PATENT DOCUMENTS

| 4,029,963 A | 6/1977 | Alvarez et al. |
| 5,247,559 A | 9/1993 | Ohtsuchi et al. |
| 6,016,356 A | 1/2000 | Ito et al. |

(Continued)

FOREIGN PATENT DOCUMENTS

| JP | H03-041933 A | 2/1991 |
| JP | H05-237081 A | 9/1993 |

(Continued)

OTHER PUBLICATIONS

Li et al., Implementation of dual-energy technique for virtual monochromatic and linearly mixed CBCTs, Sep. 18, 2012, Med. Phys. vol. 39 , pp. 6056-6064 (Year: 2012).*

(Continued)

*Primary Examiner* — Christine S. Kim
(74) *Attorney, Agent, or Firm* — Venable LLP (57) ABSTRACT

An image processing apparatus comprises an acquisition unit for acquiring low-energy information and high-energy information from a plurality of images that are obtained by emitting radiation toward an object, a calculation unit for calculating an effective atomic number and a surface density from the low-energy information and the high-energy information, and a generation unit for generating an image that includes color information based on the effective atomic number and the surface density.

22 Claims, 7 Drawing Sheets

(56) References Cited

U.S. PATENT DOCUMENTS

| | | | |
|---|---|---|---|
| 8,041,096 B2 | 10/2011 | Bernhardt et al. | |
| 8,090,181 B2 | 1/2012 | Omi | |
| 8,654,921 B2 | 2/2014 | Cho | |
| 8,942,347 B2 | 1/2015 | Cho | |
| 9,778,211 B2 | 10/2017 | Tsuyuki | |
| 2004/0028181 A1* | 2/2004 | Charles, Jr. | A61B 6/505 378/92 |
| 2006/0109949 A1* | 5/2006 | Tkaczyk | A61B 6/032 378/4 |
| 2007/0076842 A1 | 4/2007 | Tkaczyk et al. | |
| 2007/0237288 A1 | 10/2007 | Tkaczyk et al. | |
| 2008/0192898 A1* | 8/2008 | VanMetter | G06T 11/008 378/98.9 |
| 2009/0285468 A1 | 11/2009 | Omi | |
| 2010/0027867 A1 | 2/2010 | Bernhardt et al. | |
| 2012/0148133 A1 | 6/2012 | Chen et al. | |
| 2013/0101089 A1 | 4/2013 | Cho | |
| 2013/0121465 A1 | 5/2013 | Cho | |
| 2013/0182821 A1 | 7/2013 | Tsuyuki | |
| 2015/0323474 A1 | 11/2015 | Case et al. | |
| 2020/0406061 A1* | 12/2020 | McKnight | A61B 6/463 |
| 2021/0110583 A1* | 4/2021 | Lee | G06T 11/008 |
| 2021/0128096 A1* | 5/2021 | Konno | A61B 6/5205 |
| 2021/0267563 A1* | 9/2021 | Sattarivand | A61B 6/482 |

FOREIGN PATENT DOCUMENTS

| | | |
|---|---|---|
| JP | H08-076302 A | 3/1996 |
| JP | 2008-272476 A | 11/2008 |
| JP | 2009-279042 A | 12/2009 |
| JP | 2012-125409 A | 7/2012 |
| JP | 2012-245142 A | 12/2012 |
| JP | 2013-085967 A | 5/2013 |
| JP | 2013-144038 A | 7/2013 |
| JP | 2014-166351 A | 9/2014 |
| JP | 2014-239840 A | 12/2014 |
| WO | 2009/107770 A1 | 9/2009 |

OTHER PUBLICATIONS

Aug. 28, 2018 International Search Report in International Patent Appln. No. PCT/JP2018/026121.

Aug. 25, 2021 European Search Report in European Patent Appln. No. 18864534.5.

Nov. 5, 2021 Indian Official Action in Indian Patent Appln. No. 202047018643.

Feb. 20, 2023 Japanese Official Action in Japanese Patent Appln. No. 2022-062546.

* cited by examiner

IMAGE PROCESSING APPARATUS, IMAGE PROCESSING METHOD, AND PROGRAM

CROSS-REFERENCE TO RELATED APPLICATIONS

This application is a Continuation of International Patent Application No. PCT/JP2018/026121, filed Jul. 11, 2018, which claims the benefit of Japanese Patent Application No. 2017-196397, filed Oct. 6, 2017, both of which are hereby incorporated by reference herein in their entirety.

BACKGROUND OF THE INVENTION

Field of the Invention

The present invention relates to an image processing apparatus, an image processing method, and a program.

Background Art

As imaging apparatuses that are used for medical image diagnosis and nondestructive inspection using radiation such as X-rays, radiation imaging apparatuses using a Flat Panel Detector (hereinafter abbreviated as FPD) that is made from a semiconductor material are becoming popular. One example of imaging methods using the FPD is energy subtraction. In energy subtraction, a plurality of images that are formed using radioactive rays having mutually different levels of energy are acquired by emitting radioactive rays at different tube voltages a plurality of times, for example. By performing computation on the images, processing for dividing an image of an object into a bone image and a soft tissue image can be performed, for example. PTL1 proposes a technology for reducing noise of the bone image and the soft tissue image by performing image processing for varying frequency characteristics of image signals.

When catheter surgery or the like is performed using the FPD, fluoroscopic radiography is performed. In fluoroscopic radiography, low dose radiation is used to reduce the exposure dose. However, if the dose of radiation is reduced, quantum noise of the radiation increases, and noise of images divided from an image of the object increases. The technology described in PTL1 does not mention a reduction of the noise, and there is demand that various measures be taken for this issue. The present invention provides a technology for improving quality of an image generated using radiation at a plurality of levels of energy.

CITATION LIST

Patent Literature

PTL1: Japanese Patent Laid-Open No. 8-76302

SUMMARY OF THE INVENTION

In view of the above-described problem, provided is an image processing apparatus including an acquisition unit configured to acquire low-energy information and high-energy information from a plurality of images that are obtained by emitting radiation toward an object, a calculation unit configured to calculate an effective atomic number and a surface density from the low-energy information and the high-energy information, and a generation unit configured to generate an image that includes color information based on the effective atomic number and the surface density.

Further features of the present invention will become apparent from the following description of exemplary embodiments with reference to the attached drawings.

DESCRIPTION OF THE EMBODIMENTS

The following describes embodiments of the present invention with reference to the accompanying drawings. Through various embodiments, similar elements are denoted with the same reference signs, and a redundant description thereof is omitted. The embodiments can be appropriately changed or combined. In the following description, radiation includes α-rays, β-rays, γ-rays, etc. that are beams formed by particles (including photons) that are emitted through radioactive decay, as well as beams that have substantially equivalent or higher levels of energy, such as X-rays, particle beams, and cosmic rays.

First Embodiment

Figure 1:
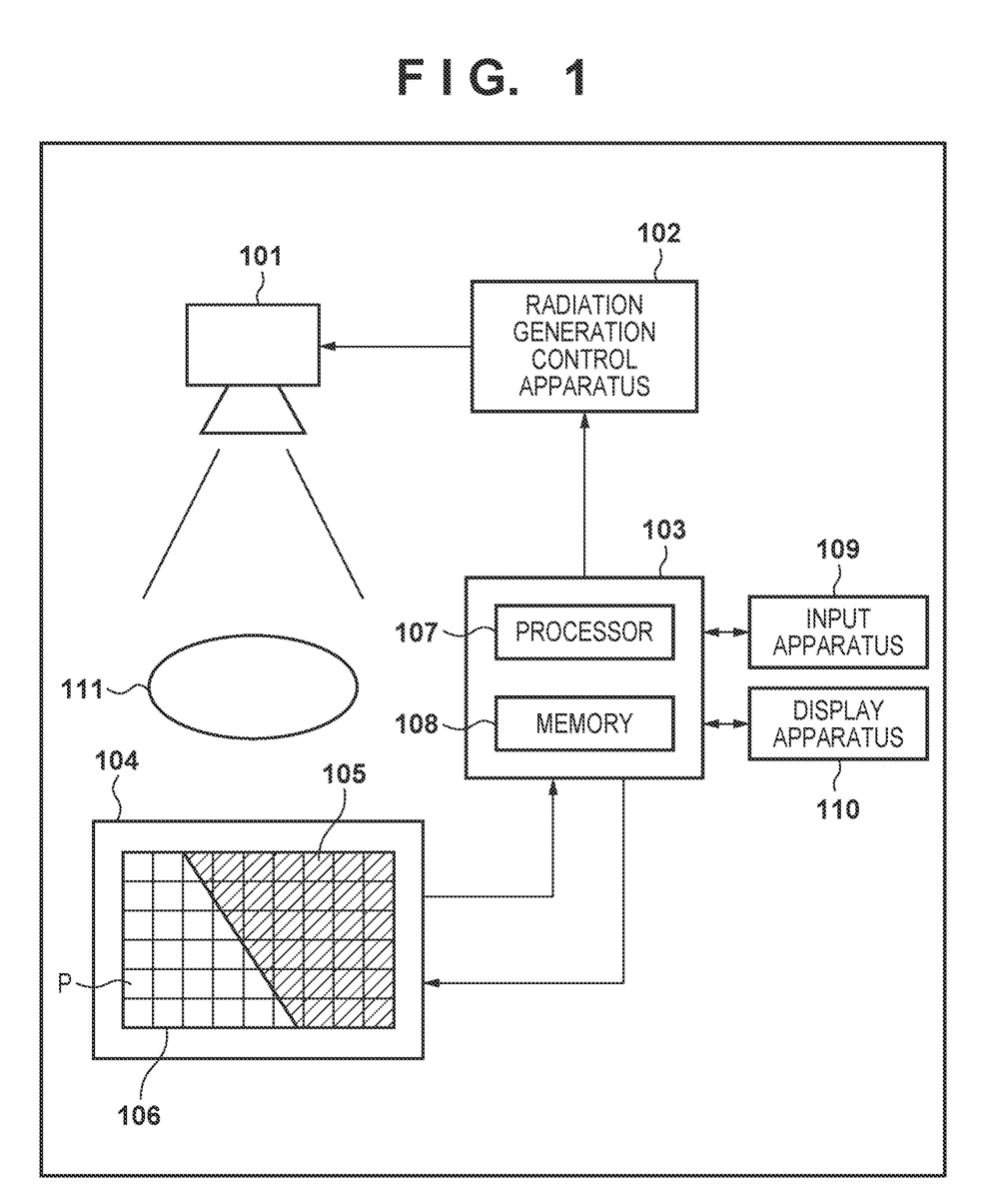
FIG. 1 is a diagram showing an example of a configuration of a radiation imaging system of each embodiment.

FIG. 1 shows a block diagram of a radiation imaging system according to the present embodiment. The radiation imaging system is used for still image capturing, such as general image capturing performed in medical diagnosis, and moving image capturing, such as fluoroscopic radiography, for example. The radiation imaging system is constituted by a radiation generating apparatus 101, a radiation generation control apparatus 102, a control apparatus 103, and a radiation imaging apparatus 104.

The radiation generation control apparatus 102 controls the radiation generating apparatus 101 to emit radiation toward the radiation imaging apparatus 104. The radiation imaging apparatus 104 is constituted by a scintillator 105 that converts radiation to visible light and a two-dimensional detector 106 that detects visible light. The two-dimensional detector 106 is a sensor in which pixels P that detect radiation quanta are arranged in an array constituted by X columns and Y rows, and outputs image information.

The control apparatus 103 controls other apparatuses in the radiation imaging system. Furthermore, as described later in detail, the control apparatus 103 performs image processing for generating a moving image based on a plurality of images that are obtained by emitting radiation at a plurality of levels of energy toward the same object. Therefore, the control apparatus 103 also functions as an image processing apparatus. Alternatively, functions of the control apparatus 103 relating to image processing may also be implemented as a separate image processing apparatus. For example, a configuration may also be employed in which images acquired by the control apparatus 103 are transferred to a separate image processing apparatus via medical PACS, and an image is displayed after energy subtraction processing is performed by this image processing apparatus.

The control apparatus 103 is a computer that includes a processor 107 and a memory 108. The processor 107 is constituted by a CPU, for example, and the memory 108 is constituted by a ROM and a RAM, for example. Processing performed by the control apparatus 103 is executed as a result of the processor 107 executing a program read into the memory 108. Alternatively, processing performed by the control apparatus 103 may also be executed by a dedicated circuit, such as an ASIC or a FPGA.

An input apparatus 109 and a display apparatus 110 are connected to the control apparatus 103. The input apparatus 109 is an apparatus for accepting input from a user of the radiation imaging system, and is constituted by a keyboard, a mouse, a touch pad, etc., for example. The display apparatus 110 is an apparatus for displaying information to the user of the radiation imaging system, and is constituted by a display, etc., for example. The input apparatus 109 and the display apparatus 110 may be configured together as a touch screen.

Figure 2:
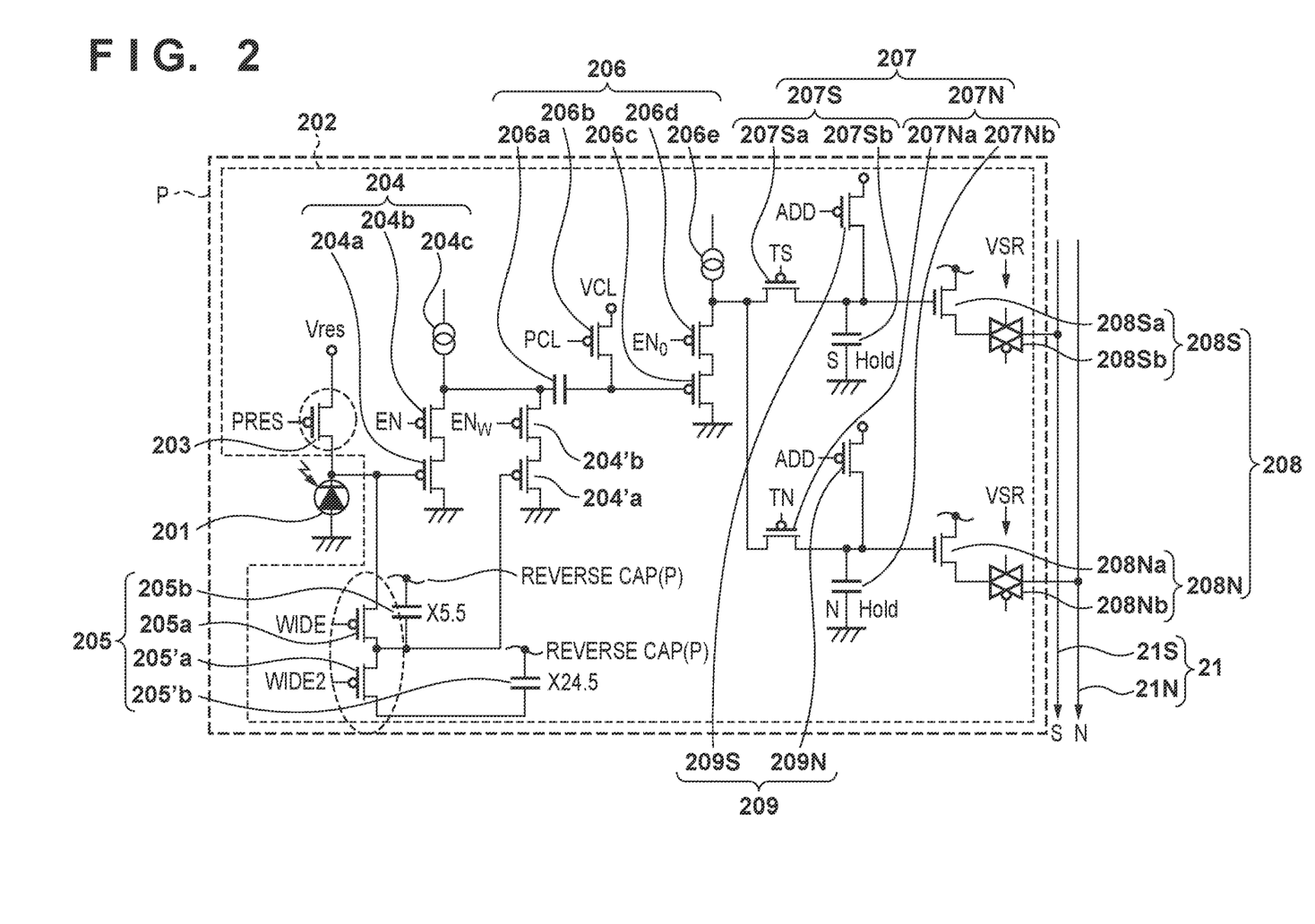
FIG. 2 is a diagram showing an example of a configuration of a pixel of each embodiment.

FIG. 2 shows an equivalent circuit schematic of a pixel P shown in FIG. 1. The pixel P includes a photoelectric conversion element 201 and an output circuit unit 202. The photoelectric conversion element 201 may be typically a photodiode. The output circuit unit 202 includes an amplifier circuit unit 204, a clamping circuit unit 206, a sample hold circuit unit 207, and a selection circuit unit 208.

The photoelectric conversion element 201 includes a charge storage unit. The charge storage unit is connected to the gate of a MOS transistor 204a of the amplifier circuit unit 204. The source of the MOS transistor 204a is connected to a current source 204c via a MOS transistor 204b. The MOS transistor 204a and the current source 204c constitute a source follower circuit. The MOS transistor 204b is an enable switch that is switched ON to cause the source follower circuit enter an operating state, when an enable signal EN supplied to the gate of the MOS transistor 204b is changed to an active level.

In the example shown in FIG. 2, the charge storage unit of the photoelectric conversion element 201 and the gate of the MOS transistor 204a constitute a common node. This node functions as a charge voltage conversion unit that converts a charge stored in the charge storage unit to a voltage. That is, a voltage V (=Q/C) that is determined by a charge Q stored in the charge storage unit and a capacitance value C of the charge voltage conversion unit appears in the charge voltage conversion unit. The charge voltage conversion unit is connected to a reset potential Vres via a reset switch 203. When a reset signal PRES is changed to an active level, the reset switch 203 is switched ON and the potential of the charge voltage conversion unit is reset to the reset potential Vres.

The clamping circuit unit 206 performs clamping on noise that is output by the amplifier circuit unit 204 according to the reset potential of the charge voltage conversion unit, by using a clamp capacitor 206a. That is, the clamping circuit unit 206 is a circuit for cancelling this noise from a signal that is output from the source follower circuit according to a charge generated through photoelectric conversion in the photoelectric conversion element 201. This noise includes kTC noise at the time of reset. Clamping is performed by switching a MOS transistor 206b ON by changing a clamp signal PCL to an active level, and thereafter switching the MOS transistor 206b OFF by changing the clamp signal PCL to a non-active level. The output side of the clamp capacitor 206a is connected to the gate of a MOS transistor 206c. The source of the MOS transistor 206c is connected to a current source 206e via a MOS transistor 206d. The MOS transistor 206c and the current source 206e constitute a source follower circuit. The MOS transistor 206d is an enable switch that is switched ON to cause the source follower circuit enter an operating state, when an enable signal $EN_0$ supplied to the gate of the MOS transistor 206d is changed to an active level.

A signal that is output from the clamping circuit unit 206 according to the charge generated through photoelectric conversion in the photoelectric conversion element 201 is written as an optical signal into a capacitor 207Sb via a switch 207Sa as a result of an optical signal sampling signal TS being changed to an active level. A signal that is output from the clamping circuit unit 206 when the MOS transistor 206b is switched ON immediately after the potential of the charge voltage conversion unit is reset is a clamp voltage. This noise signal is written into a capacitor 207Nb via a switch 207Na as a result of a noise sampling signal TN being changed to an active level. This noise signal includes an offset component of the clamping circuit unit 206. The switch 207Sa and the capacitor 207Sb constitute a signal sample hold circuit 207S and the switch 207Na and the capacitor 207Nb constitute a noise sample hold circuit 207N. The sample hold circuit unit 207 includes the signal sample hold circuit 207S and the noise sample hold circuit 207N.

When a drive circuit unit drives a row selection signal to an active level, the signal (optical signal) held by the capacitor 207Sb is output to a signal line 21S via a MOS transistor 208Sa and a row selection switch 208Sb. At the same time, the signal (noise) held by the capacitor 207Nb is output to a signal line 21N via a MOS transistor 208Na and a row selection switch 208Nb. The MOS transistor 208Sa constitutes a source follower circuit together with a constant current source (not shown) provided on the signal line 21S. Likewise, the MOS transistor 208Na constitutes a source follower circuit together with a constant current source (not shown) provided on the signal line 21N. The signal line 21S and the signal line 21N will be collectively referred to as a signal line 21. The MOS transistor 208Sa and the row selection switch 208Sb constitute a signal selection circuit unit 208S, and the MOS transistor 208Na and the row selection switch 208Nb constitute a noise selection circuit unit 208N. The selection circuit unit 208 includes the signal selection circuit unit 208S and the noise selection circuit unit 208N.

The pixel P may also include an addition switch 209S that adds optical signals of a plurality of pixels P adjacent to each other. In an addition mode, an addition mode signal ADD is changed to an active level, and the addition switch 209S is switched ON. As a result, capacitors 207Sb of adjacent pixels P are connected to each other via the addition switch 209S, and optical signals are averaged. Likewise, the pixel P may also include an addition switch 209N that adds noise of a plurality of pixels P adjacent to each other. When the addition switch 209N is switched ON, capacitors 207Nb of adjacent pixels P are connected to each other via the addition switch 209N, and noise is averaged. An addition unit 209 includes the addition switch 209S and the addition switch 209N.

The pixel P may also include a sensitivity changing unit 205 for changing sensitivity. For example, the pixel P may include a first sensitivity change switch 205a, a second sensitivity change switch 205'a, and circuit elements accompanying these switches. When a first change signal WIDE is changed to an active level, the first sensitivity change switch 205a is switched ON, and the capacitance value of a first additional capacitor 205b is added to the capacitance value of the charge voltage conversion unit. Thus, sensitivity of the pixel P is lowered. When a second change signal WIDE2 is changed to an active level, the second sensitivity change switch 205'a is switched ON, and the capacitance value of a second additional capacitor 205'b is added to the capacitance value of the charge voltage conversion unit. Thus, sensitivity of the pixel P is further lowered. If a function for lowering sensitivity of the pixel P is added as described above, a larger quantity of light can be received, and the dynamic range is widened. If the first change signal WIDE is changed to the active level, a MOS transistor 204'a may also be caused to perform a source follower operation, instead of the MOS transistor 204a, by changing an enable signal $EN_W$ to an active level. The MOS transistor 204'a is connected to the clamp capacitor 206a via a MOS transistor 204'b.

The radiation imaging apparatus 104 reads the output of the above-described pixel P, converts the output to a digital value using an AD converter (not shown), and then transfers an image to the control apparatus 103. In a case in which the radiation imaging system captures a moving image, images are periodically transferred as frames from the radiation imaging apparatus 104 to the control apparatus 103. That is, a moving image is transferred from the radiation imaging apparatus 104 to the control apparatus 103. In the present embodiment, a moving image means chronological images.

Figure 3:
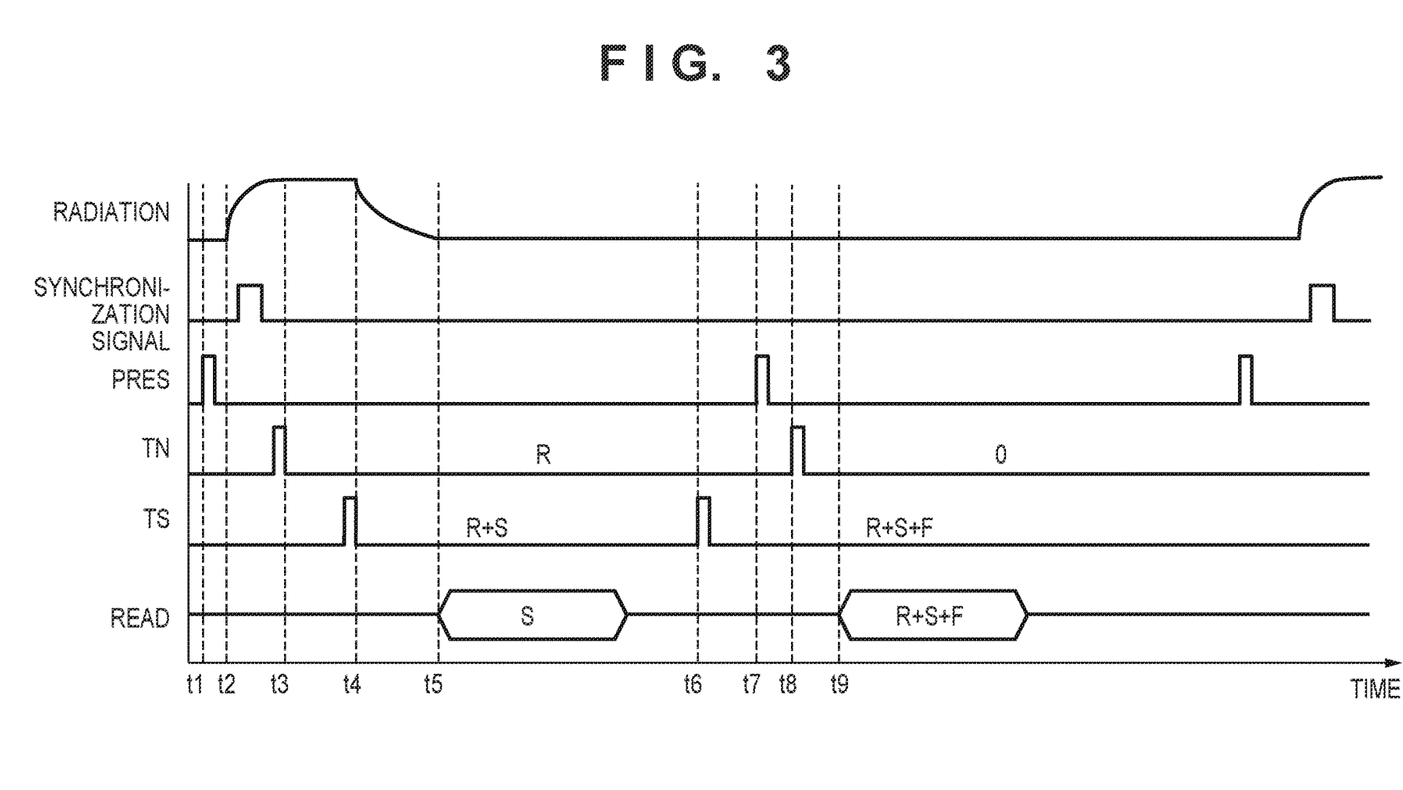
FIG. 3 is a diagram showing a frame operation of each embodiment.

Driving timings for performing energy subtraction in the radiation imaging system of the present embodiment will be described with reference to FIG. 3. "Radiation" shows the dose of radiation emitted toward the radiation imaging apparatus 104. "Synchronization signal" is a signal that is supplied by the control apparatus 103 to the radiation imaging apparatus 104. "PRES" is the reset signal described with reference to FIG. 2. "TS" is the optical signal sampling signal TS described with reference to FIG. 2. "TN" is the noise sampling signal TN described with reference to FIG. 2.

At time t1, the control apparatus 103 resets the photoelectric conversion element 201. At time t2, the control apparatus 103 starts emission of radiation. The tube voltage of radiation ideally has a rectangular waveform, but it takes finite times for the tube voltage to rise and fall. In particular, if pulsed radiation is emitted for a short period of time, the tube voltage has a waveform as shown in FIG. 3, which cannot be considered a rectangular waveform. That is, energy of the radiation varies between a rise period (time t2 to time t3), a stable period (time t3 to time t4), and a fall period (time t4 to time t5). As described above, in the present embodiment, radiation is emitted at a plurality of levels of energy in a single emission of radiation.

At time t3 (the end of the radiation rise period), the control apparatus 103 performs sampling using the noise sample hold circuit 207N. As a result, a signal R that is obtained using radiation of the rise period is held by the noise sample hold circuit 207N. At time t4 (the end of the radiation stable period), the control apparatus 103 performs sampling using the signal sample hold circuit 207S. As a result, a sum of the signal R and a signal S that is obtained using radiation of the stable period is held by the signal sample hold circuit 207S. At time t5, a reading circuit (not shown) of the radiation imaging apparatus 104 transmits, as an image, a difference between a signal read from the signal line 21N and a signal read from the signal line 21S to the control apparatus 103. Since the signal R is held by the noise sample hold circuit 207N and the sum of the signal R and the signal S is held by the signal sample hold circuit 207S, the reading circuit outputs the signal S.

After emission of radiation and reading of the signal S are complete, at time t6, the control apparatus 103 performs sampling using the signal sample hold circuit 207S again. As a result, a sum of the signal R, the signal S, and a signal F that is obtained using radiation of the fall period is held by the signal sample hold circuit 207S. At time t7, the control apparatus 103 resets the photoelectric conversion element 201. At time t8, the control apparatus 103 performs sampling using the signal sample hold circuit 207S again. As a result, a signal (in this example, 0) at the time of reset is held by the signal sample hold circuit 207S. At time t9, the reading circuit of the radiation imaging apparatus 104 transmits, as an image, a difference between a signal read from the signal line 21N and a signal read from the signal line 21S to the control apparatus 103. Since 0 is held by the noise sample hold circuit 207N and the sum of the signal R, the signal S, and the signal F is held by the signal sample hold circuit 207S, the reading circuit outputs the sum of the signal R, the signal S, and the signal F. The control apparatus 103 can calculate a sum of the signal R obtained using radiation of the rise period and the signal F obtained using radiation of the fall period, by calculating a difference between the two transmitted images. An image represented by the signal S and an image represented by the sum of the signal R and the signal F correspond to images that are obtained using radiation at mutually different levels of energy. Therefore, the control apparatus 103 can perform energy subtraction by performing computation on the images.

Timings for resetting the sample hold circuit unit 207 and the photoelectric conversion element 201 are determined using a synchronization signal 307 that indicates that emission of radiation from the radiation generating apparatus 101 is started. As a method for detecting the start of emission of radiation, a configuration may be employed in which the tube current of the radiation generating apparatus 101 is measured, and it is determined whether or not the current value is higher than a preset threshold value. Alternatively, a configuration may also be employed in which, after the photoelectric conversion element 201 is reset, signals are repeatedly read from the pixel P, and it is determined whether or not the pixel value is higher than a preset threshold value. A configuration may also be employed in which a radiation detector other than the two-dimensional detector 106 is incorporated in the radiation imaging apparatus 104, and it is determined whether or not a measurement value obtained by the radiation detector is higher than a preset threshold value. In any of these cases, after a prescribed period has elapsed from input of the synchronization signal 307, the radiation imaging apparatus 104 performs sampling using the signal sample hold circuit 207S, performs sampling using the noise sample hold circuit 207N, and resets the photoelectric conversion element 201.

Figure 4:
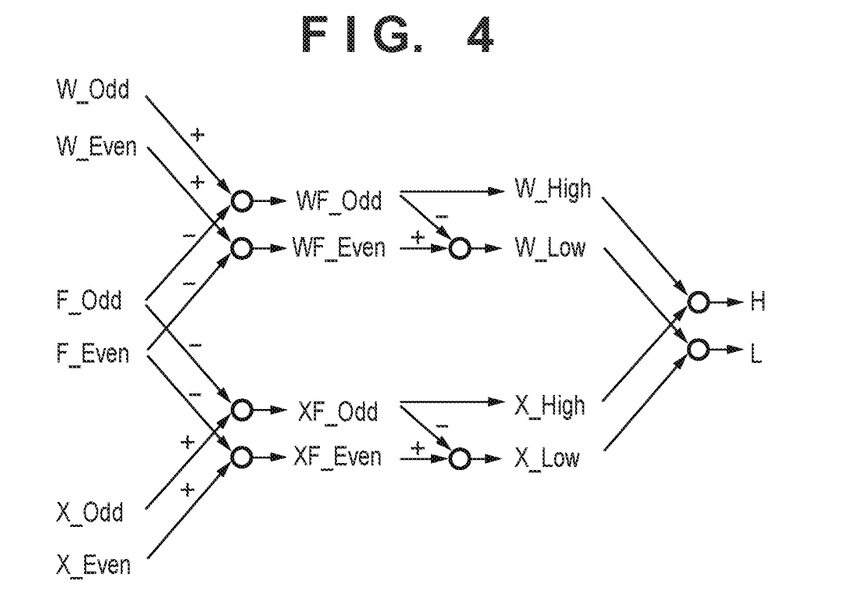
FIG. 4 is a diagram showing some operations of a control apparatus of each embodiment.

Next, a method of energy subtraction will be described. Energy subtraction in the present embodiment is divided into three steps, namely, correction, signal processing, and image processing. A correction method performed in energy subtraction processing in the present embodiment will be described with reference to FIG. 4. The control apparatus 103 acquires the two images described with reference to FIG. 3 by performing imaging without emitting radiation toward the radiation imaging apparatus 104. An image represented by the signal S is denoted as F_Odd, and an image represented by the sum of the signal R, the signal S, and the signal F is denoted as F_Even. These images correspond to fixed pattern noise (FPN) of the radiation imaging apparatus 104.

Next, the control apparatus 103 acquires the two images described with reference to FIG. 3 by performing imaging by emitting radiation toward the radiation imaging apparatus 104 in a state in which an object 111 is not arranged. An image represented by the signal S is denoted as W_Odd, and an image represented by the sum of the signal R, the signal S, and the signal F is denoted as W_Even. These images correspond to sums of the fixed pattern noise (FPN) of the radiation imaging apparatus 104 and the signals obtained using radiation. By subtracting F_Odd from W_Odd and subtracting F_Even from W_Even, WF_Odd and WF_Even from which the FPN has been removed are obtained.

WF_Odd is an image represented by the signal S obtained using radiation of the stable period, and WF_Even is an image represented by the sum of the signal R, the signal S, and the signal F respectively obtained using radiation of the rise period, the stable period, and the fall period. Radiation of the stable period has higher energy than radiation of the rise period and radiation of the fall period. Accordingly, the control apparatus 103 takes WF_Odd as a high-energy image W_High in a case in which the object 111 is absent, and takes an image that is obtained by subtracting WF_Odd from WF_Even (i.e., an image represented by a sum of the signal R and the signal F) as a low-energy image W_Low in the case in which the object 111 is absent.

Next, the control apparatus 103 acquires the two images described with reference to FIG. 3 for each frame period by capturing a moving image by emitting radiation toward the radiation imaging apparatus 104 in a state in which the object 111 is arranged. Thus, the control apparatus 103 acquires a plurality of images obtained by emitting radiation at a plurality of levels of energy toward the same object 111. An image represented by the signal S is denoted as X_Odd, and an image represented by the sum of the signal R, the signal S, and the signal F is denoted as X_Even. These images correspond to sums of the fixed pattern noise (FPN) of the radiation imaging apparatus 104 and the signals obtained using radiation. By subtracting F_Odd from X_Odd and subtracting F_Even from X_Even, XF_Odd and XF_Even from which the FPN has been removed are obtained. Thereafter, similarly to the case in which the object 111 is absent, the control apparatus 103 takes XF_Odd as a high-energy image X_High in a case in which the object 111 is present. Also, the control apparatus 103 takes an image that is obtained by subtracting XF_Odd from XF_Even (i.e., an image represented by the sum of the signal R and the signal F) as a low-energy image X_Low in the case in which the object 111 is present.

When d represents the thickness of the object 111, μ represents the linear attenuation coefficient of the object 111, $I_0$ represents the pixel value in the case in which the object 111 is absent, and I represents the pixel value in the case in which the object 111 is present, the following equation holds.

$$I = I_0 \exp(\mu d) \qquad (1)$$

The following equation is obtained by transforming equation (1).

$$I/I_0 = \exp(\mu d) \qquad (2)$$

The right side of equation (2) indicates the attenuation ratio of the object 111. The attenuation ratio of the object 111 is a real number between 0 to 1. Therefore, the control apparatus 103 computes an image L at an attenuation ratio of low energy by dividing the low-energy image X_Low in the case in which the object 111 is present by the low-energy image W_Low in the case in which the object 111 is absent. Likewise, the control apparatus 103 computes an image H at an attenuation ratio of high energy by dividing the high-energy image X_High in the case in which the object 111 is present by the high-energy image W_High in the case in which the object 111 is absent.

Figure 5:
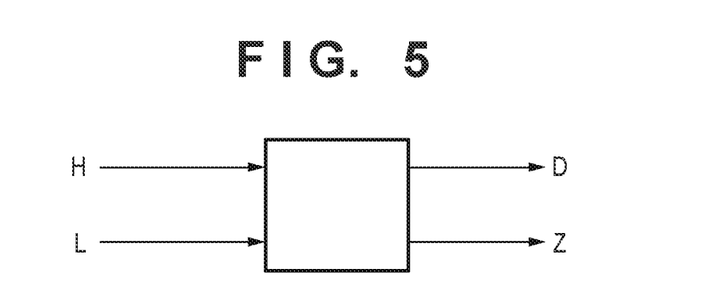
FIG. 5 is a diagram showing some operations of a control apparatus of a first embodiment.

Next, a signal processing method performed in energy subtraction in the present embodiment will be described with reference to FIG. 5. The control apparatus 103 computes an image that represents an effective atomic number Z and an image that represents a surface density D from the image L and the image H obtained through the processing shown in FIG. 4. The image L and the image H are based on the plurality of images that the control apparatus 103 acquired from the radiation imaging apparatus 104, and accordingly the control apparatus 103 generates an image representing the effective atomic number Z and a second image representing the surface density D using the plurality of images. The effective atomic number Z is an equivalent atomic number of a mixture. The surface density D is a product of the density [g/cm$^3$] of the object 111 and the thickness [cm] of the object 111, and the dimension of the surface density D is [g/cm$^2$].

When E represents energy of radiation photons, N(E) represents the photon number at the energy E, Z represents the effective atomic number, D represents the surface density, μ(Z, E) represents the mass attenuation coefficient at the effective atomic number Z and the energy E, and $I/I_0$ represents the attenuation ratio, the following equation holds.

$$I/I_0 = \frac{\int_0^\infty N(E)\exp\{-\mu(Z, E)D\}EdE}{\int_0^\infty N(E)EdE} \qquad (3)$$

The photon number N(E) at the energy E is the spectrum of radiation. The spectrum of radiation is obtained through simulation or actual measurement. Also, the mass attenuation coefficient μ(Z, E) at the effective atomic number Z and the energy E is obtained from a database of NIST (National Institute of Standards and Technology), for example. Namely, the attenuation ratio $I/I_0$ at a given effective atomic number Z, a given surface density D, and a given spectrum N(E) of radiation can be calculated.

When $N_L(E)$ represents the spectrum of radiation of the rise period and the fall period and $N_H(E)$ represents the spectrum of radiation of the stable period, the following two equations hold.

$$L = \frac{\int_0^\infty N_L(E)\exp\{-\mu(Z, E)D\}EdE}{\int_0^\infty N_L(E)EdE} \qquad (4)$$

$$H = \frac{\int_0^\infty N_H(E)\exp\{-\mu(Z, E)D\}EdE}{\int_0^\infty N_H(E)EdE} \quad (5)$$

Equations (4) are nonlinear simultaneous equations. By solving the simultaneous equations using the Newton-Raphson method, for example, the control apparatus 103 can compute the image representing the effective atomic number Z and the image representing the surface density D from the image L at the attenuation ratio of low energy and the image H at the attenuation ratio of high energy.

Figure 6:
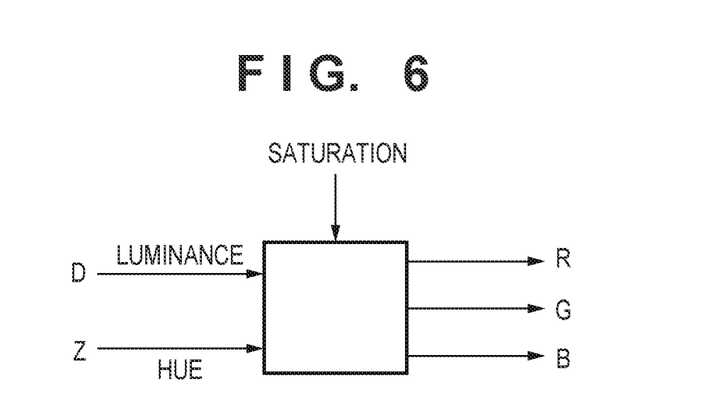
FIG. 6 is a diagram showing some operations of the control apparatus of the first embodiment.

An image processing method performed in energy subtraction processing in the present embodiment will be described with reference to FIG. 6. In image processing performed in the present embodiment, the control apparatus 103 sets values of two parameters that constitute a frame based on the image representing the effective atomic number Z and the image representing the surface density D, and sets the value of one parameter that constitutes the frame based on a setting set by a user. As described above, the image representing the effective atomic number Z and the image representing the surface density D are generated based on frames of a plurality of images. Accordingly, the control apparatus 103 sets values of the two parameters based on the frames of the plurality of images obtained by emitting radiation at a plurality of levels of energy toward the same object 111. The control apparatus 103 generates at least some frames of a moving image using values of these three parameters.

In the present embodiment, the moving image constituted by a plurality of images is a color image, and the three parameters are components of a color space. The color space is an HLS color space or an HSV color space, for example. The following describes an example in which the color space is an HLS color space. The HLS color space is constituted by three components, namely, hue, saturation, and luminance. The control apparatus 103 sets hue and luminance based on the above-described plurality of images and sets saturation based on a setting set by a user. Note that saturation of all frames of the moving image does not necessarily have to be set based on a setting set by a user, and a configuration is also possible in which saturation of some frames is set based on a setting set by a user.

For example, the control apparatus 103 sets the value of hue based on the image representing the effective atomic number Z and sets the value of luminance based on the image representing the surface density D. Specifically, the control apparatus 103 converts the effective atomic number Z to hue using a function (e.g., a linear function) according to which the minimum value and the maximum value of the effective atomic number Z are respectively mapped to the minimum value and the maximum value of hue. Luminance is set in a similar manner. Further, the control apparatus 103 uses an initial value as saturation. The initial value of saturation may be stored in the memory 108 when the control apparatus 103 is manufactured, or may be set by the user via the input apparatus 109, for example.

The control apparatus 103 converts hue, saturation, and luminance set as described above into an RGB value. Examples of conversion methods used for the HLS color space include a cylindrical model and a conic model. According to the conic model for example, an RGB value is obtained from hue H, saturation S, and luminance L using the following equations.

$$\text{Max} = L + \frac{S}{2} \quad (5)$$

$$\text{Min} = L - \frac{S}{2} \quad (6)$$

$$(R, G, B) = \begin{cases} (\text{Max} = \text{Min}, \text{Max} = \text{Min}, \text{Max} = \text{Min}) & \text{if } H \text{ is undefined} \\ \left(\text{Max}, \text{Min} + (\text{Max} - \text{Min}) \times \frac{H}{60}, \text{Min}\right) & \text{if } 0 \le H < 60 \\ \left(\text{Min} + (\text{Max} - \text{Min}) \times \frac{120 - H}{60}, \text{Max}, \text{Min}\right) & \text{if } 60 \le H < 120 \\ \left(\text{Min}, \text{Max}, \text{Min} + (\text{Max} - \text{Min}) \times \frac{H - 120}{60}\right) & \text{if } 120 \le H < 180 \\ \left(\text{Min}, \text{Min} + (\text{Max} - \text{Min}) \times \frac{240 - H}{60}, \text{Max}\right) & \text{if } 180 \le H < 240 \\ \left(\text{Min} + (\text{Max} - \text{Min}) \times \frac{H - 240}{60}, \text{Min}, \text{Max}\right) & \text{if } 240 \le H < 300 \\ \left(\text{Max}, \text{Min}, \text{Min} + (\text{Max} - \text{Min}) \times \frac{360 - H}{60}\right) & \text{if } 300 \le H < 360 \end{cases}$$

Saturation S is a real number between 0 and 1. If saturation S=0 for example, Max=L and Min=L and accordingly the RGB value is (L, L, L) irrespective of the value of hue H. Namely, a monochrome image to which only luminance L is reflected is obtained. In contrast, as saturation S gets closer to 1, information regarding hue H is more strongly reflected, and therefore materials constituting the object can be more easily distinguished based on colors. On the other hand, noise of hue increases, and therefore it becomes harder to see a difference in luminance.

If the radiation imaging apparatus 104 is installed in a C-arm used for fluoroscopy in catheter surgery or the like, fluoroscopy is sometimes continuously performed for one hour or longer. In order to reduce the risk of damage, such as a burn injury, due to exposure to radiation, the dose per frame of fluoroscopy is reduced. If the dose is reduced, quantum noise of radiation increases, and accordingly noise of the image L at the attenuation ratio of low energy and noise of the image H at the attenuation ratio of high energy increase. As a result, noise of the effective atomic number Z increases and accordingly noise of hue also increases, and information regarding the object that has been recognized as a difference in luminance may be hidden by the noise of hue and become invisible. That is, there is a risk that visibility will be impaired. In such a case, noise can be reduced by lowering saturation. Therefore, the radiation imaging system according to the present embodiment is configured such that the value of saturation can be changed while a moving image is displayed.

Figure 7:
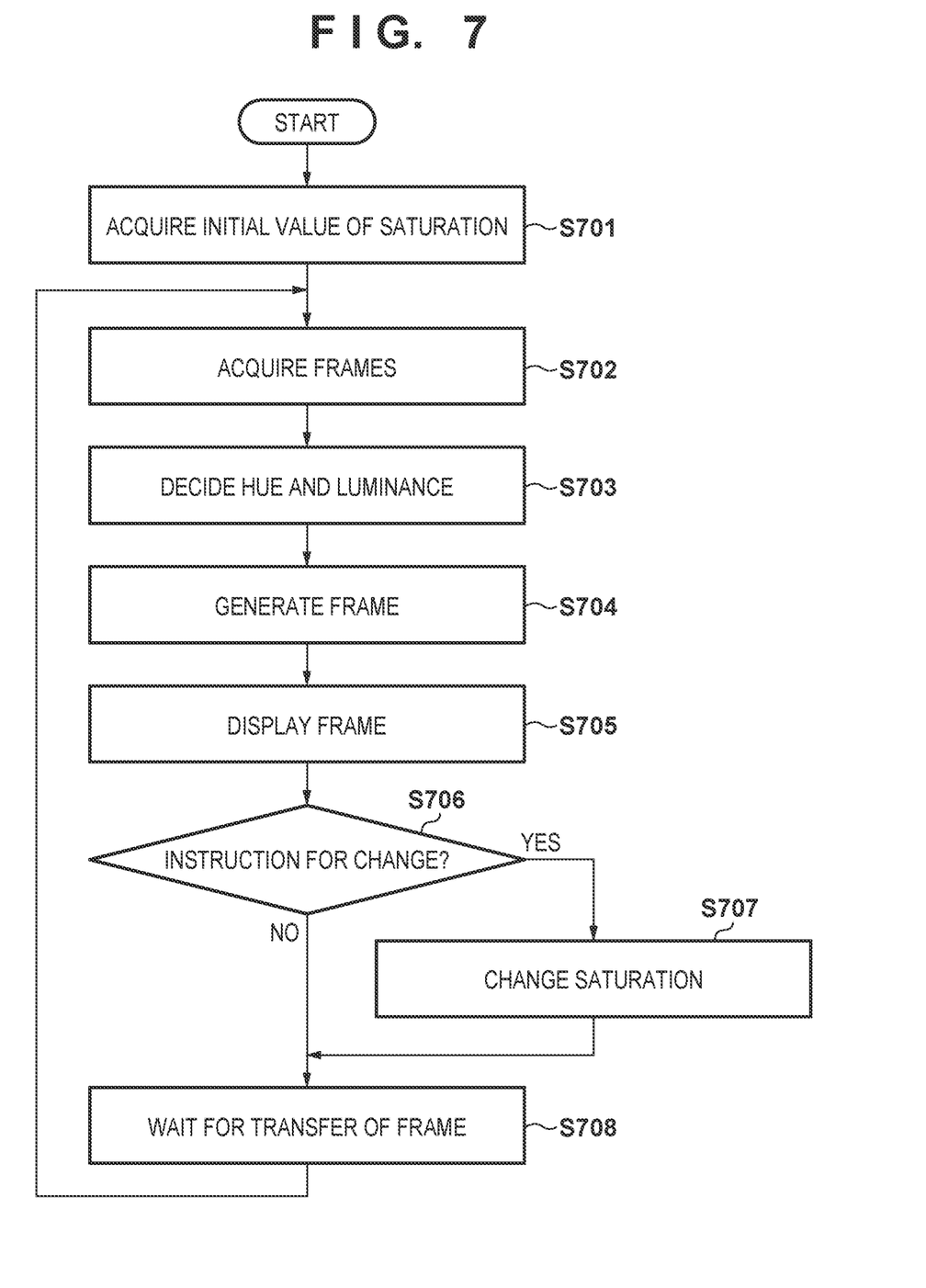
FIG. 7 is a diagram showing some operations of the control apparatus of the first embodiment.

An image processing method performed by the control apparatus 103 will be described with reference to FIG. 7. This processing is executed as a result of the processor 107 executing a program read into the memory 108, for example. In step S701, the control apparatus 103 acquires an initial value of saturation. As described above, the initial value of saturation may be set by a user or may be stored in the memory 108 during manufacture.

In step S702, the control apparatus 103 acquires frames of two images from the radiation imaging apparatus 104. Specifically, an acquisition unit of the control apparatus 103 acquires low-energy information and high-energy information from a plurality of images that are obtained by emitting radiation toward the object 111 as described above. An image represented by the low-energy information and an image represented by the high-energy information are the frames of the two images.

In step S703, the control apparatus 103 sets values of hue and luminance that constitute a frame of a moving image based on the frames of the two images as described above. Here, a calculation unit of the control apparatus 103 calculates an effective atomic number and a surface density from the low-energy information and the high-energy information as described above. A setting unit of the control apparatus 103 sets values for hue and luminance based on the effective atomic number and the surface density. Also, the setting unit of the control apparatus 103 sets a value for saturation. Generally, the setting unit of the control apparatus 103 sets values for at least two parameters of hue, luminance, and/or saturation based on the effective atomic number and the surface density. Also, the setting unit of the control apparatus 103 sets a preset value, for at least one parameter of hue, luminance, and/or saturation. In step S704, the control apparatus 103 generates a frame using the set values of hue, luminance, and saturation. Namely, a generation unit of the control apparatus 103 generates an image that includes color information based on the effective atomic number and the surface density. In step S705, the control apparatus 103 causes the display apparatus 110 to display the generated frame.

In step S706, the setting unit of the control apparatus 103 determines whether an instruction for changing the value of saturation is acquired from the user. If the instruction is acquired ("YES" in step S706), the control apparatus 103 advances the processing to step S707, and if the instruction is not acquired ("NO" in step S706), the control apparatus 103 advances the processing to step S708. The instruction from the user is given via the input apparatus 109, for example. The same value may be set for saturation of each pixel of the frame by the user. For example, the user may uniformly change saturation of all pixels by using a GUI such as a slide bar.

In step S707, the setting unit of the control apparatus 103 acquires the instruction for changing the value of saturation from the user and stores the changed value in the memory 108. In step S708, the control apparatus 103 waits for the next frames of the plurality of images to be transferred from the radiation imaging apparatus 104. After the next frames are transferred, the control apparatus 103 returns the processing to step S702, and the next frame of the moving image is generated and displayed. If step S707 has been executed, the setting unit of the control apparatus 103 sets saturation to the changed value. The generation unit of the control apparatus 103 generates the following frames of the moving image using the changed value of saturation.

In the above-described example, the control apparatus 103 sets the value of hue based on the effective atomic number Z, sets the value of luminance based on the surface density D, and sets the value of saturation based on a setting set by a user. Alternatively, the control apparatus 103 may also set the value of luminance based on the image L at the attenuation ratio of low energy or the image H at the attenuation ratio of high energy, instead of the surface density D. Alternatively, the control apparatus 103 may also set the value of luminance based on the high-energy image X_High in the case in which the object 111 is present, the low-energy image X_Low in the case in which the object 111 is present, or a sum of these images. The control apparatus 103 may also set the value of luminance based on a logarithm of the attenuation ratio L of low energy or a logarithm of the attenuation ratio H of high energy. That is, the control apparatus 103 is only required to set the value of luminance based on frames of a plurality of images, and may set the value of luminance by directly using these frames or by using images obtained by converting these frames. The same also applies to setting of hue.

In the above-described example, the value of hue and the value of luminance are set based on frames of images, and the value of saturation is set based on a setting set by a user. Alternatively, a configuration is also possible in which the value of saturation and the value of luminance are set based on frames of images, and the value of hue is set based on a setting set by a user. Further, a configuration is also possible in which the value of hue and the value of saturation are set based on frames of images, and the value of luminance is set based on a setting set by a user. In a case in which an HSV color space is used for generating a frame, any of the values of hue, saturation, and brightness may be configured to be set by the user.

In the present embodiment, processing for reducing noise of hue may be performed by applying a recursive filter or the like. In this case, image lag may occur in a portion in which the object 111 has moved. Therefore, movement of the image of the object 111 may be detected and the coefficient of the recursive filter may be reduced. As a method for detecting movement of the image of the object 111, there is a method of determining that the object 111 has moved if the absolute value of a difference in the pixel value between the current frame and the immediately preceding frame is larger than a preset threshold value.

If such processing is applied, noise of hue is not reduced in the portion in which the object 111 has moved, and accordingly visibility is impaired. Therefore, the control apparatus 103 may change saturation S of a region in which movement of the image of the object 111 is detected. Assume that $D[t]$ represents the surface density in the t-th frame, $D'[t-1]$ represents the surface density in the t−1-th frame after application of the recursive filter, and $S[t]$ represents saturation S in the t-th frame. The control apparatus 103 sets saturation using the following equations.

$$S[t]=S(|D[t]-D'[t-1]|\leq T)$$

$$S[t]=0(|D[t]-D'[t-1]|>T) \qquad (7)$$

Thus, the control apparatus 103 sets saturation of each pixel in a region of the moving image that satisfies $|D[t]-D'[t-1]|>T$ to a value that differs from saturation of each pixel in regions other than this region. Generally, the setting unit of the control apparatus 103 sets saturation of each pixel in a region of a generated image that satisfies a predetermined condition to a value that differs from saturation of each pixel in regions other than this region. The condition $|D[t]-D'[t-1]|>T$ is a condition regarding a change (movement) in the image of the object 111 in a time direction. Through the above-described processing, impairment of visibility due to noise of hue can be prevented while suppressing image lag in a case in which the object 111 has moved.

The condition for setting saturation to a different value may include a condition regarding a change in the image of the object 111 in a spatial direction or a condition regarding a statistic (e.g., a spatial frequency) of the image, as well as a condition regarding a change in the image of the object 111 in the time direction. Namely, the predetermined condition may include a condition that relates to at least any of a change in the image of the object 111 in the spatial direction, a change in the image of the object 111 in the time direction, and/or a statistic of the image. In the case of a condition regarding a change in the image of the object 111 in the spatial direction, a case is detected in which the image includes an edge or the like. Namely, the control apparatus 103 sets saturation of each pixel in a region of the moving image that satisfies a predetermined condition to a value that differs from saturation of each pixel in regions other than this region.

Furthermore, a configuration is also possible in which, if the moving image (i.e., the image to be generated) satisfies a predetermined condition, the setting unit of the control apparatus 103 sets saturation to a value that differs from the value set by the user. In such a case, the control apparatus 103 may uniformly set saturation to zero or set saturation to half the value set by the user. As described above, the predetermined condition may include a condition that relates to at least any of a change in the image of the object 111 in the spatial direction, a change in the image of the object 111 in the time direction, and/or a statistic of the image.

Second Embodiment

A radiation imaging system according to a second embodiment will be described. The configuration (FIGS. 1 and 2) of the radiation imaging system is the same as that in the first embodiment. The operations (FIG. 3) performed by the control apparatus 103 to acquire a plurality of images from the radiation imaging apparatus 104 and the operations (FIG. 4) for computing the image L at the attenuation ratio of low energy and the image H at the attenuation ratio of high energy are also the same as those in the first embodiment.

Figure 8:
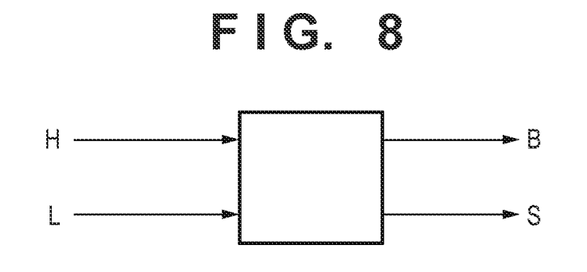
FIG. 8 is a diagram showing some operations of a control apparatus of a second embodiment.

A signal processing method performed in energy subtraction in the present embodiment will be described with reference to FIG. 8. The control apparatus 103 computes an image B that represents the thickness of a bone and an image S that represents the thickness of a soft tissue from the image L and the image H obtained through the processing shown in FIG. 4. The image L and the image H are based on the plurality of images that the control apparatus 103 acquired from the radiation imaging apparatus 104, and accordingly the control apparatus 103 generates the image B representing the thickness of the bone and the image S representing the thickness of the soft tissue using the plurality of images.

Assume that E represents energy of radiation photons, N(E) represents the photon number at the energy E, B represents the thickness of the bone, and S represents the thickness of the soft tissue. Also, $\mu_B(E)$ represents the linear attenuation coefficient of the bone at the energy E, $\mu_S(E)$ represents the linear attenuation coefficient of the soft tissue at the energy E, and $I/I_0$ represents the attenuation ratio. At this time, the following equation holds.

$$I/I_0 = \frac{\int_0^\infty N(E)\exp\{-\mu_B(E)B - \mu_S(E)S\}EdE}{\int_0^\infty N(E)EdE} \quad (8)$$

The photon number N(E) at the energy E is the spectrum of radiation. The spectrum of radiation is obtained through simulation or actual measurement. Also, the linear attenuation coefficient $\mu_B(E)$ of the bone at the energy E and the linear attenuation coefficient $\mu_S(E)$ of the soft tissue at the energy E are obtained from a database of NIST, for example. Namely, the attenuation ratio $I/I_0$ at a given thickness B of the bone, a given thickness S of the soft tissue, and a given spectrum N(E) of radiation can be calculated.

When $N_L(E)$ represents the spectrum of radiation of the rise period and the fall period and $N_H(E)$ represents the spectrum of radiation of the stable period, the following two equations hold.

$$L = \frac{\int_0^\infty N_L(E)\exp\{-\mu_B(E)B - \mu_S(E)S\}EdE}{\int_0^\infty N_L(E)EdE} \quad (9)$$

$$H = \frac{\int_0^\infty N_H(E)\exp\{-\mu_B(E)B - \mu_S(E)S\}EdE}{\int_0^\infty N_H(E)EdE}$$

Equations (9) are nonlinear simultaneous equations. By solving the simultaneous equations using the Newton-Raphson method, for example, the control apparatus 103 can compute the image representing the thickness B of the bone and the image representing the thickness S of the soft tissue from the image L at the attenuation ratio of low energy and the image H at the attenuation ratio of high energy.

Although the control apparatus 103 computes the image representing the thickness B of the bone and the image representing the thickness S of the soft tissue in the present embodiment, generally, the control apparatus 103 may compute an image that represents the thickness of a substance and an image that represents the thickness of another substance. For example, the control apparatus 103 may compute an image representing the thickness I of a contrast medium and an image representing the thickness S of the soft tissue.

Figure 9:
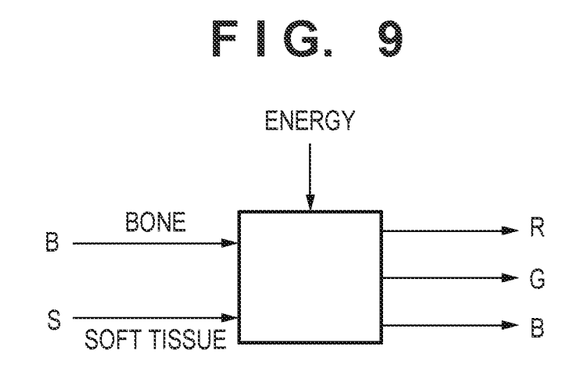
FIG. 9 is a diagram showing some operations of the control apparatus of the second embodiment.

An image processing method performed in energy subtraction processing in the present embodiment will be described with reference to FIG. 9. In image processing performed in the present embodiment, the control apparatus 103 sets values of two parameters that constitute a frame based on the image representing the thickness B of the bone and the image representing the thickness S of the soft tissue, and sets the value of one parameter that constitutes the frame based on a setting set by a user. As described above, the image representing the thickness B of the bone and the image representing the thickness S of the soft tissue are generated based on frames of a plurality of images. Accordingly, the control apparatus 103 sets values of the two parameters based on the frames of the plurality of images obtained by emitting radiation at a plurality of levels of energy toward the same object 111. The control apparatus 103 generates at least some frames of a moving image using values of these three parameters.

In the present embodiment, the moving image is a monochrome moving image, the parameters set based on the frames of the plurality of images are the thickness B of the bone and the thickness S of the soft tissue, and the parameter set by the user is energy of a virtual monochromatic radiation image. Each frame of the moving image is a virtual monochromatic radiation image. For example, when $E_V$ represents energy of virtual monochromatic radiation, a virtual monochromatic radiation image V is obtained using the following equation. A monochrome frame is generated by setting the value of V for each of R, G, and B of the frame.

$$V = \exp\{-\mu_B(E_V)B - \mu_S(E_V)S\} \quad (10)$$

Virtual monochromatic radiation images are used in Dual Energy CT in which energy subtraction and 3-D reconstruction are used in combination. If a virtual monochromatic radiation image is generated in fluoroscopic radiography performed using a small dose, the contrast-to-noise ratio (CNR) may be reduced by noise of the bone image. The linear attenuation coefficient $\mu_B(E)$ of the bone is larger than the linear attenuation coefficient $\mu_S(E)$ of the soft tissue, and therefore is likely to affect noise of the virtual monochromatic radiation image V. If the CNR is reduced, visibility is impaired.

The linear attenuation coefficient $\mu_B(E)$ of the bone is larger than the linear attenuation coefficient $\mu_S(E)$ of the soft tissue. The difference between these coefficients decreases as the energy $E_V$ of virtual monochromatic radiation increases. Accordingly, an increase in noise of the virtual monochromatic radiation image due to noise of the bone image is suppressed. On the other hand, as the energy $E_V$ of virtual monochromatic radiation decreases, the difference between $\mu_B(E)$ and $\mu_S(E)$ increases, and accordingly the contrast of the virtual monochromatic radiation image increases. Therefore, the radiation imaging system according to the present embodiment is configured such that the energy $E_V$ of the virtual monochromatic radiation image can be changed while a moving image is displayed.

Figure 10:
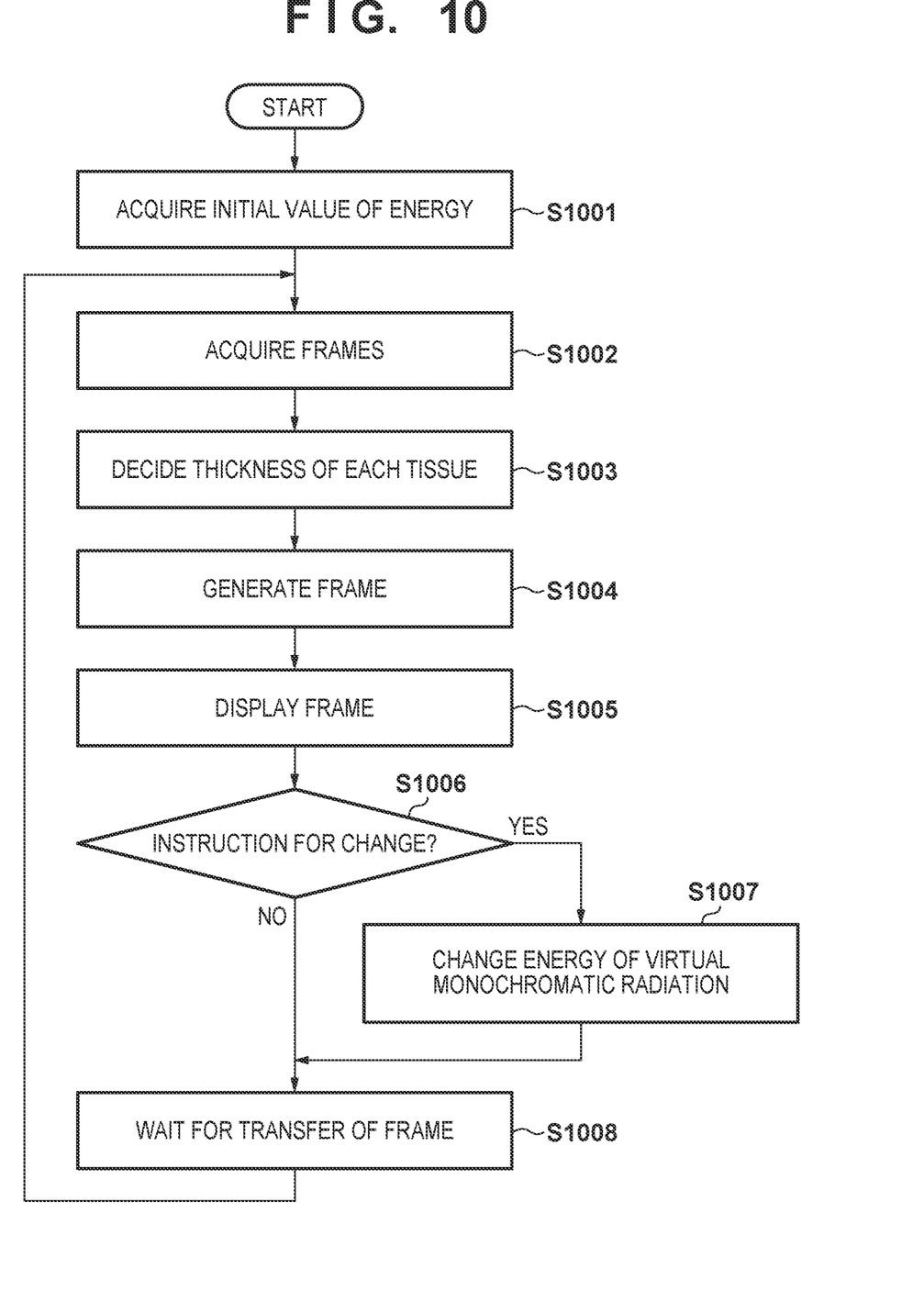
FIG. 10 is a diagram showing some operations of the control apparatus of the second embodiment.

An image processing method performed by the control apparatus 103 will be described with reference to FIG. 10. This processing is executed as a result of the processor 107 executing a program read into the memory 108, for example. In step S1001, the control apparatus 103 acquires an initial value of the energy $E_V$ of the virtual monochromatic radiation image. The initial value of the energy $E_V$ of the virtual monochromatic radiation image may be set by the user as described above, or may be stored in the memory 108 during manufacture.

In step S1002, the control apparatus 103 acquires frames of two images from the radiation imaging apparatus 104. Specifically, the acquisition unit of the control apparatus 103 acquires low-energy information and high-energy information from a plurality of images that are obtained by emitting radiation toward the object 111 as described above. An image represented by the low-energy information and an image represented by the high-energy information are the frames of the two images. In step S1003, the calculation unit of the control apparatus 103 calculates the thickness B of the bone and the thickness S of the soft tissue that constitute a frame of a moving image based on the frames of the two images. Generally, the calculation unit of the control apparatus 103 calculates information indicating the thickness of a first tissue and information indicating the thickness of a second tissue from the low-energy information and the high-energy information, as described above. Also, the setting unit of the control apparatus 103 sets energy $E_V$ of a virtual monochromatic radiation image to be used for generating an image to a preset value. In step S1004, the generation unit of the control apparatus 103 generates a frame using the calculated thickness B of the bone, the calculated thickness S of the soft tissue, and the set value of the energy $E_V$ of the virtual monochromatic radiation image. Namely, the generation unit of the control apparatus 103 generates an image based on information indicating the thickness of a first tissue and information indicating the thickness of a second tissue. In step S1005, the control apparatus 103 causes the display apparatus 110 to display the generated frame.

In step S1006, the control apparatus 103 determines whether an instruction for changing the value of energy $E_V$ of the virtual monochromatic radiation image is received from the user. If the instruction is received ("YES" in step S1006), the control apparatus 103 advances the processing to step S1007, and if the instruction is not received ("NO" in step S1006), the control apparatus 103 advances the processing to step S1008. The instruction from the user is given via the input apparatus 109, for example. The same value may be set for energy $E_V$ of the virtual monochromatic radiation image with respect to each pixel of the frame by the user. For example, the user may uniformly change energy $E_V$ of the virtual monochromatic radiation image with respect to all pixels by using a GUI such as a slide bar.

In step S1007, the control apparatus 103 acquires the instruction for changing the value of energy $E_V$ of the virtual monochromatic radiation image from the user and stores the changed value in the memory 108. In step S1008, the control apparatus 103 waits for the next frames of the plurality of images to be transferred from the radiation imaging apparatus 104. After the next frames are transferred, the control apparatus 103 returns the processing to step S1002, and the next frame of the moving image is generated and displayed. If step S1007 has been executed, the control apparatus 103 generates the following frames of the moving image using the changed value of energy $E_V$ of the virtual monochromatic radiation image.

In the above-described example, the control apparatus 103 generates a virtual monochromatic radiation image using the thickness B of the bone and the thickness S of the soft tissue. Alternatively, the control apparatus 103 may also calculate the effective atomic number Z and the surface density D as is the case with the first embodiment, and generate a virtual monochromatic radiation image using the effective atomic number Z and the surface density D. Alternatively, the control apparatus 103 may also generate a composite radiation image by compositing a plurality of virtual monochromatic radiation images generated using a plurality of levels of energy $E_V$. A composite radiation image is an image that is to be obtained if radiation of a given spectrum is emitted.

In the present embodiment, processing for reducing noise of the bone image and noise of the soft tissue image may be performed by applying a recursive filter or the like. In this case, image lag may occur in a portion in which the object 111 has moved. Therefore, movement of the image of the object 111 may be detected and the coefficient of the recursive filter may be reduced. As a method for detecting movement of the image of the object 111, there is a method of determining that the object 111 has moved if the absolute value of a difference in the pixel value between the current frame and the immediately preceding frame is larger than a preset threshold value.

If such processing is applied, noise of the bone image and noise of the soft tissue image are not reduced in the portion in which the object 111 has moved, and therefore it is desirable to reduce energy $E_V$ of the virtual monochromatic radiation image to increase contrast. On the other hand, since noise is not reduced in the portion in which the object 111 has moved, it is desirable to increase energy $E_V$ of the virtual monochromatic radiation image to reduce noise. Therefore, the control apparatus 103 may change energy $E_V$ in a region in which movement of the image of the object 111 is detected. Assume that S[t] represents the thickness of the soft tissue in the t-th frame, S'[t−1] represents the thickness of the soft tissue in the t−1-th frame after application of the recursive filter, and $E_V$[t] represents energy $E_V$ in the t-th frame. The control apparatus 103 sets energy using the following equations.

$$EV[t]=E_L(|S[t]-S'[t-1]|\leq T)$$

$$EV[t]=E_H(|S[t]-S'[t-1]|>T) \quad (11)$$

Namely, the control apparatus 103 sets energy of each pixel in a region of the moving image that satisfies |S[t]−S'[t−1]|>T to a value that differs from energy of each pixel in regions other than this region. The condition |S[t]−S'[t−1]|>T is a condition regarding a change (movement) in the image of the object 111 in a time direction. Through the above-described processing, the CNR of the virtual monochromatic radiation image can be improved while suppressing image lag in a case in which the object 111 has moved.

The condition for setting energy $E_V$ to a different value may include a condition regarding a change in the image of the object 111 in a spatial direction or a condition regarding a statistic (e.g., a spatial frequency) of the image, as well as a condition regarding a change in the image of the object 111 in the time direction. In the case of a condition regarding a change in the image of the object 111 in the spatial direction, a case is detected in which the image includes an edge or the like. Namely, the control apparatus 103 sets energy of each pixel in a region of the moving image that satisfies a predetermined condition to a value that differs from energy of each pixel in regions other than this region.

Furthermore, a configuration is also possible in which, if the moving image satisfies a predetermined condition, the control apparatus 103 sets energy $E_V$ to a value that differs from the value set by the user. In such a case, the control apparatus 103 may uniformly set energy to a predetermined value or set saturation to half the value set by the user. As described above, the predetermined condition may include a condition that relates to at least any of a change in the image of the object 111 in the spatial direction, a change in the image of the object 111 in the time direction, and/or a statistic of the image.

Variations

In the first embodiment and the second embodiment, the radiation imaging apparatus 104 is an indirect radiation sensor using a scintillator. Alternatively, the radiation imaging apparatus 104 may also be a direct radiation sensor using a direct conversion material such as CdTe, for example.

The radiation generating apparatus 101 utilizes a passive change in the tube voltage. Alternatively, the radiation generating apparatus 101 may also actively change the tube voltage. A configuration is also possible in which energy of radiation emitted toward the radiation imaging apparatus 104 is varied by temporally switching a filter of the radiation generating apparatus 101, for example.

In the above-described examples, energy subtraction is performed by varying energy of radiation emitted toward the radiation imaging apparatus 104. Alternatively, a method may also be employed in which two sensors are layered so that the spectrum of radiation changes between radiation detected by a front sensor and radiation detected by a rear sensor, for example. Alternatively, a plurality of images that differ from each other in energy may also be acquired using a photon counting sensor that counts the number of radiation quanta for each level of energy.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

With the above-described embodiments, the quality of an image generated using radiation at a plurality of levels of energy is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
at least one of (a) one or more processors connected to one or more memories storing a program including instructions executed by the one or more processors and (b) circuitry, configured to perform functions comprising:
(1) obtaining an effective atomic number and a surface density using low-energy information and high-energy information that are obtained by emitting radiation toward an object; and
(2) generating an image that includes color information using images related to the effective atomic number and the surface density,
wherein the image is generated by applying (a) a first value of a parameter to a first region that satisfies a predetermined condition in the images related to the effective atomic number and the surface density and (b) a second value of the parameter to a second region in the images related to the effective atomic number and the surface density, with the second value being different from the first value and the second region being different from the first region.

2. The image processing apparatus according to claim 1, wherein the at least one of (a) the one or more processors and (b) the circuitry is further configured to perform a function of setting values for at least two parameters of hue, luminance, and/or saturation based on the effective atomic number and the surface density.

3. The image processing apparatus according to claim 2, wherein a preset value is set for at least one parameter of hue, luminance, and/or saturation.

4. The image processing apparatus according to claim 3, wherein a preset value is set for saturation.

5. The image processing apparatus according to claim 2, wherein an instruction for changing a value of saturation is acquired from a user, and a changed value for saturation is set.

6. The image processing apparatus according to claim 2, wherein if the image including color information to be generated satisfies a predetermined condition, a value that differs from a value set by a user is set for saturation.

7. The image processing apparatus according to claim 2, wherein for saturation of each pixel in a region of the image including color information to be generated that satisfies a predetermined condition, a value that differs from saturation of each pixel in a region of the images related to the effective atomic number and the surface density other than the region satisfying the predetermined condition is set.

8. The image processing apparatus according to claim 1, wherein the predetermined condition includes a condition that relates to at least any of a change in the images related to the effective atomic number and the surface density in a spatial direction, a change in the images related to the effective atomic number and the surface density in a time direction, and/or a statistic of the images related to the effective atomic number and the surface density.

9. The image processing apparatus according to claim 1, wherein radiation is emitted at a plurality of levels of energy in a single emission of radiation.

10. An image processing apparatus comprising:
at least one of (a) one or more processors connected to one or more memories storing a program including instructions executed by the one or more processors and (b) circuitry, configured to perform functions comprising:
(1) obtaining information indicating a thickness of a first tissue and information indicating a thickness of a second tissue using low-energy information and high-energy information that are obtained by emitting radiation toward an object; and
(2) generating a virtual monochromatic radiation image using the information indicating the thickness of the first tissue and the information indicating the thickness of the second tissue,
wherein the virtual monochromatic radiation image is generated by applying (a) a first value of a parameter to a first region that satisfies a predetermined condition in the information indicating the thickness of the first tissue and the information indicating the thickness of the second tissue and (b) a second value of the parameter to a second region in the information indicating the thickness of the first tissue and the information indicating the thickness of the second tissue, the second value being different from the first value and the second region being different from the first region.

11. The image processing apparatus according to claim 10, wherein the at least one of (a) the one or more processors and (b) the circuitry is further configured to perform a function of setting a preset value for energy of the virtual monochromatic radiation image that is used for generating the virtual monochromatic radiation image including color information.

12. The image processing apparatus according to claim 10, wherein the virtual monochromatic radiation image is generated using information obtained by performing energy subtraction processing.

13. The image processing apparatus according to claim 10, wherein the predetermined condition includes a condition that relates to at least one of (a) a change in the information indicating the thickness of the first tissue and the information indicating the thickness of the second tissue in a spatial direction, (b) a change in the information indicating the thickness of the first tissue and the information indicating the thickness of the second tissue in a time direction, or (c) a statistic of the information indicating the thickness of the first tissue and the information indicating the thickness of the second tissue.

14. An image processing method comprising:
obtaining an effective atomic number and a surface density using low-energy information and high-energy information that are obtained by emitting radiation toward an object; and
generating an image that includes color information using images related to the effective atomic number and the surface density, wherein, in the generating, (a) a first value of a parameter is applied to a first region that satisfies a predetermined condition in the images related to the effective atomic number and the surface density and (b) a second value of the parameter is applied to a second region in the images related to the effective atomic number and the surface density, the second value being different from the first value and the second region being different from the first region.

15. A non-transitory storage medium storing a program for causing a computer to perform the image processing method according to claim 14.

16. An image processing method comprising:
obtaining information indicating a thickness of a first tissue and information indicating a thickness of a second tissue using low-energy information and high-energy information that are obtained by emitting radiation toward an object; and
generating a virtual monochromatic radiation image using the information indicating the thickness of the first tissue and the information indicating the thickness of the second tissue,
wherein, in the generating, (a) a first value of a parameter is applied to a first region that satisfies a predetermined condition in the information indicating the thickness of the first tissue and the information indicating the thickness of the second tissue and (b) a second value of the parameter is applied to a second region in the information indicating the thickness of the first tissue and the information indicating the thickness of the second tissue, the second value being different from the first value and the second region being different from the first region.

17. A non-transitory storage medium storing a program for causing a computer to perform the image processing method according to claim 16.

18. An image processing apparatus comprising:
at least one of (a) one or more processors connected to one or more memories storing a program including instructions executed by the one or more processors and (b) circuitry, configured to perform functions comprising:
(1) obtaining information by performing energy subtraction processing using low-energy information and high-energy information that are obtained by emitting radiation toward an object; and
(2) generating a virtual monochromatic radiation image using the information obtained by performing the energy subtraction processing, wherein the virtual monochromatic radiation image is generated by applying (a) a first value of a parameter to a first region that satisfies a predetermined condition in the information obtained by performing the energy subtraction processing and (b) a second value of the parameter to a second region in the information obtained by performing the energy subtraction processing, the second value being different from the first value and the second region being different from the first region.

19. The image processing apparatus according to claim 18, wherein the information obtained by performing the energy subtraction processing includes (a) an effective atomic number image and a surface density image or (b) information indicating a thickness of a first tissue and information indicating a thickness of a second tissue, and wherein the virtual monochromatic radiation image is generated using the information obtained by performing the energy subtraction processing.

20. The image processing apparatus according to claim 18, wherein the predetermined condition includes a condition that relates to at least one of (a) a change in the information obtained by performing the energy subtraction processing in a spatial direction, (b) a change in the information obtained by performing the energy subtraction processing in a time direction, or (c) a statistic of the information obtained by performing the energy subtraction processing.

21. An image processing method comprising:

obtaining information by performing energy subtraction processing using low-energy information and high-energy information that are obtained by emitting radiation toward an object; and generating a virtual monochromatic radiation image using the information obtained by performing the energy subtraction processing, wherein, in the generating, (a) a first value of a parameter is applied to a first region that satisfies a predetermined condition in the information obtained by performing the energy subtraction processing and (b) a second value of the parameter is applied to a second region in the information obtained by performing the energy subtraction processing, the second value being different from the first value and the second region being different from the first region.

22. A non-transitory storage medium storing a program for causing a computer to perform the image processing method according to claim 21.

* * * * *